(12) United States Patent
Sander

(10) Patent No.: US 7,197,948 B2
(45) Date of Patent: Apr. 3, 2007

(54) METHOD OF DOSING LIQUID VOLUMES AND APPARATUS FOR THE EXECUTION OF THE METHOD

(75) Inventor: Dietmar Sander, Geesthacht (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 11/259,390

(22) Filed: Oct. 26, 2005

(65) Prior Publication Data

US 2006/0090576 A1    May 4, 2006

(30) Foreign Application Priority Data

Oct. 29, 2004   (DE) .................. 10 204 052 832

(51) Int. Cl.
*G01N 1/00* (2006.01)

(52) U.S. Cl. .................................. 73/863.01

(58) Field of Classification Search ............... None
See application file for complete search history.

(56) References Cited

U.S. PATENT DOCUMENTS

| | | | |
|---|---|---|---|
| 5,499,545 A * | 3/1996 | Kimura et al. ......... | 73/864.18 |
| 5,537,880 A * | 7/1996 | Takeda et al. ......... | 73/864.25 |
| 6,112,605 A * | 9/2000 | Papen et al. ......... | 73/864.22 |
| 6,370,942 B1 | 4/2002 | Dunfee et al. ......... | 73/37 |
| 2001/0047692 A1 * | 12/2001 | Lipscomb et al. ...... | 73/864.25 |
| 2002/0018841 A1 | 12/2002 | Salje ................. | 702/50 |
| 2004/0089051 A1 | 5/2004 | Comenisch ............ | 73/1.05 |
| 2005/0095723 A1 * | 5/2005 | DiTrolio et al. ...... | 436/180 |

FOREIGN PATENT DOCUMENTS

| | | |
|---|---|---|
| EP | 1 059 535 A | 12/2000 |
| EP | 1 150 105 A2 | 4/2001 |

\* cited by examiner

*Primary Examiner*—Robert Raevis
(74) *Attorney, Agent, or Firm*—Vidas, Arrett & Steinkraus, P.A.

(57) ABSTRACT

Method for dosing liquid volumes, wherein a sample pickup portion with a pickup volume, the boundary of which is perforated with a liquid passage guiding to the outside and a gas passage, is dipped into a liquid with the liquid passage, a negative pressure is suddenly applied to the gas passage, which is generated by a gas displacement system, a drive of the gas displacement system is readjusted such that a constant negative working pressure exists in the sample pickup portion, the taken sample volume is detected with the aid of the readjusted driving path of the drive, the detected taken volume is compared with a predetermined value of the volume that is to be taken, when the predetermined value is reached by the taken volume, the negative pressure applied on the sample pickup portion is suddenly abated, the sample pickup portion with the liquid passage is pulled out of the liquid the sample pickup portion with the liquid passage is directed towards a releasing location, one ore more flow parameters is/are determined from the values of the taken volume, the negative working pressure and the time period required to take up the volume, an overpressure is applied to the gas passage of the sample pickup portion, the moment at which a volume that is to be released is released is determined with the aid of the flow parameter(s) and the overpressure, and when the moment is reached, the overpressure applied to the sample pickup portion is suddenly abated.

17 Claims, 1 Drawing Sheet

METHOD OF DOSING LIQUID VOLUMES AND APPARATUS FOR THE EXECUTION OF THE METHOD

CROSS-REFERENCE TO RELATED APPLICATIONS

Not applicable.

STATEMENT REGARDING FEDERALLY SPONSORED RESEARCH

Not applicable.

BACKGROUND OF THE INVENTION

In known plunger stroke apparatuses, a gas cushion is moved by moving a plunger in a cylinder, in order to aspirate a liquid sample into a pipette point or another sample pickup portion or to eject it from it. The volume is determined with the aid of the volume displacement of the gas cushion, which is proportional to the adjusted path of the plunger. As an adjustment member or actor unit, respectively, for moving the plunger in the cylinder, a stepping motor is used for instance, which accurately hits working points for taking up and releasing liquid, in a fashion that is independent of the working load. After reaching the working points, it is waited until the taking or releasing of the liquid is complete. The dosing is based on the fact that pressure compensation up to reaching a static balance takes place between gas cushion, liquid in the pipette point and surroundings.

From EP-A-1 150 105 a gas cushion microdosing system for dosing liquids in the microliter and sub-microliter range is known. The system has a liquid reservoir with a storage room for the liquid that is to be dosed, the boundary of which is perforated with a liquid passage guiding to the outside and a gas passage. A gas displacement system with a micro pump for pumping a gas has a connection to the gas passage. A dosing control unit for generating a negative pressure or an overpressure by actuating the micro pump and for pressurising the liquid reservoir with the negative pressure or overpressure is in interacting connection with the micro pump, in order to take up liquid through the liquid passage into the storage room or to release it from the same. The system has a pressure sensor for detecting the pressure in the gas displacement system, with which the dosing control unit is in interacting connection in order to determine the taken or released liquid volume or to regulate it towards a predetermined value. The dosing control unit controls the negative pressure or the overpressure in the gas displacement system when aspirating or releasing liquid by detecting the pressure existing therein by means of the pressure sensor and regulating the pumping rate or the volume displacement of the micro pump towards a predetermined value or course of that value, and determines the taken up or released liquid volume or regulates is towards a predetermined value, via the pumping rate or the volume displacement of the micro pump.

The determination of the released volume by knowing the pumping rate is time-critical and imprecise, in particular when smaller liquid volumes are to be released at relatively high overpressures in a free stream and the pumping rate is pressure-dependent. Even taking gas equations of state as an aid is also imprecise, by reason of the fast volume displacement for generating the overpressures, that has to be known, and thus is not suited for the determination of liquid volumes that are to be released.

Departing from this, the present invention is based on the objective to provide a method for dosing liquid volumes which enables accurate dynamic detection of the liquid volume that has been dosed. Further, the present invention is based on the objective to provide an apparatus for dosing liquid volumes, suited for practising the method.

BRIEF SUMMARY OF THE INVENTION

In the method according to the present invention for dosing liquid volumes, 1.1 a sample pickup portion with a pickup volume, the boundary of which is perforated with a liquid passage guiding to the outside and a gas passage, is dipped into a liquid with the liquid passage, 1.2 a negative pressure is suddenly applied to the gas passage, which is generated by a gas displacement system, 1.3 a drive of the gas displacement system is readjusted such that a constant negative working pressure exists in the sample pickup portion, 1.4 the taken sample volume is detected with the aid of the readjusted driving path of the drive, 1.5 the detected taken volume is compared with a predetermined value of the volume that is to be taken, 1.6 when the predetermined value is reached by the taken volume, the negative pressure applied on the sample pickup portion is suddenly abated, 1.7 the sample pickup portion with the liquid passage is pulled out of the liquid, 1.8 the sample pickup portion with the liquid passage is directed towards a releasing location, 1.9 one ore more flow parameters is/are determined from the values of the taken volume, the negative working pressure and the time period required to take up the volume, 1.10 an overpressure is applied to the gas passage of the sample pickup portion, 1.11 the moment at which a volume that is to be released is released is determined with the aid of the flow parameter(s) and the overpressure, and 1.12 when the moment is reached, the overpressure applied to the sample pickup portion is suddenly abated.

In this method, when taking up the liquid, a dynamic detection of the taken liquid volume is performed at substantially constant pressure in three phases with different pumping action: in a first phase, a negative pressure is suddenly applied to a sample pickup portion (a pipette point, for instance) in order to hit a certain working pressure as fast as possible. The volume that flows in within this period is difficult to determine and is therefore neglected. This phase ends when the working negative pressure is reached. In the following second phase, the drive of the gas displacement system is readjusted such that the working negative pressure is maintained. The volume that is taken up is directly proportional to the readjusted driving path of the drive. The second phase ends as soon as the volume that has to be taken up is taken up in the sample pickup portion. In the following third phase, the negative pressure that is applied to sample pickup portion is suddenly abated, in order to stop taking up liquid as fast as possible. The volume that flows in within this period is difficult to determine and is therefore also neglected. In principle, the liquid that is taken up can be held in the sample pickup portion by capillary forces. Optionally, the sudden decay of the negative pressure takes place until a keeping negative pressure is reached, which keeps the taken liquid in the sample pickup portion.

By the negative working pressure block profile that is applied when taking up liquid, the influence of pressure variations on the determination of the taken volume is largely suppressed. Furthermore, by applying a relatively low working pressure, a taking-up duration can be achieved which is long with respect to the phases of build-up and decay of the negative pressure. Through this, the error due to the pressure change in these phases is kept negligibly small. In addition, on account of the negative working pressure block profile, the liquid volume that has been taken up is accurately known at each moment, so that it has not to be awaited until a static pressure balance is reached. Only through this, the detection of the taken volume with the aid of the readjusted driving path is made possible. The taken volume is detected repeatedly or continuously, for instance. At the same time, one or more flow parameter(s) are determined from the negative pressure and the taking duration.

For releasing the liquid, the knowledge of the flow parameter(s) is used, which describes or describe, respectively, the volume of the liquid flown through the liquid passage per unit of time and pressure. When releasing the liquid, the volume that has been released is calculated with the aid of the flow parameters(s) and the known overpressure on the one hand, and the duration of its action on the other hand. Preferably, the overpressure is constant when releasing the liquid, so that the releasing duration for releasing a volume that has to be released can be easily calculated and the releasing can be stopped when the releasing duration is reached. When the flowing conditions are non-linear, at usual working pressures in a pipette point for instance, according to one form of realisation, the released volume is determined according to a reference pressure-volume flow curve. Through this pressure independence, the overpressure when releasing can be deliberately headed for or it must be adjusted in relatively narrow limits only, because pressure variations can be compensated. According to one form of realisation, in order to do this, volumes released in time periods at different overpressures are integrated and the releasing is stopped when the volume to be released is reached. Thus, pressure variations are adjusted for by changing the overall releasing duration.

The determination of the released volume with the aid of the flow parameter(s) favours the release of liquid volumes which is time-critical with respect to the adjustment of the pressure. This is particularly advantageous with respect to the dosing of extremely small liquid volumes in the microliter and sub-microliter range and to dosing in a free stream. However, the method according to the invention is in principle also suited for the dosing of liquid volumes in the microliter and milliliter range.

For the release, it is advantageous to have at hand a characteristics of the flow conditions in the pipette point (by at least one parameter), from which the release volume is determined from the volume flow rate and the time duration of the release when the pressure is known. The characterisation of the flow conditions—essentially coupled to the viscosity of the liquid and the cross section of the nozzle opening of the pipette point—is performed through the take-up, which normally takes place at substantially smaller negative pressures. Through this, significantly longer time intervals result, which favour the accurate determination of the pickup volumes.

The sudden applying of the negative pressure according to the feature 1.2 and optionally, as the case may be, of the overpressure according to feature 1.10, takes place through suddenly putting into operation the drive of the gas displacement system. However, it may also take place through that a gas displacement system, which has a pressure storage element, for instance, is connected to the gas passage via a valve. Accordingly, the sudden abatement of the negative pressure according to feature 1.6 or that of the overpressure according to feature 1.12 takes place by suddenly putting the drive out of operation or by closing a valve between gas passage and gas displacement system.

The readjustment of the negative pressure in the gas displacement system according to feature 1.3 takes place at repeated or continuous measurement of the negative pressure in the sample pickup portion or in the gas displacement system and controlling the drive such that a more or less constant negative pressure is established.

The detection of the taken up volume according to feature 1.4 and the comparison with a predetermined value according to feature 1.5 can also be performed repeatedly or continuously.

The flow parameter(s) according to feature 1.9 can be determined at any deliberate moment, at which the taken-up volume is determined according to feature 1.5. Preferably the flow parameter(s) is/are determined when the taken-up volume has reached the predetermined value of the volume to be taken up, according to feature 1.6.

In the method for dosing liquid volumes according to the invention 2.1 a sample pickup portion with a pickup volume, the boundary of which is perforated with a liquid passage guiding to the outside and a gas passage, is dipped into a liquid with the liquid passage, 2.2 a monotonically increasing negative pressure is applied to the gas passage, which is generated by a gas displacement system, 2.3 the course of the negative pressure in the sample pickup portion is measured, 2.4 the moment of the inflow of liquid into the sample pickup portion is detected on account of a deviation of the pressure increases in two time periods of the pressure measurement.

2.5 the negative pressure in the sample pickup portion and the gas volume in the sample pickup portion and in the gas displacement system are detected at the moment of the entrance of the liquid into the sample pickup portion, 2.6 the taken liquid volume is detected on account of the negative pressure and the gas volume at the moment of inflow and either (a) at continued monotonic operation of the drive of the gas displacement system, on account of the difference between the negative pressure that is calculated from the actual pumping rate and the time since the inflow of the liquid, and the actually measured negative pressure, or (b) when the drive is stopped at the moment of inflow, on account of the difference between the negative pressure at the moment of inflow and the actually measured negative pressure, 2.7 the detected taken volume is compared with a predetermined value of the volume that is to be taken, 2.8 when the predetermined value is reached by the taken volume, the negative pressure applied on the sample pickup portion is suddenly abated, 2.9 the sample pickup portion with the liquid passage is pulled out of the liquid.

In this method, dynamic detection of the taken liquid volume is performed when taking up the liquid at variable pressure course in three phases with different pumping action: in a first phase, a monotonically increasing negative pressure is generated after dipping a sample pickup portion (a pipette point, for instance) into a liquid, departing from an initial position of a drive of the gas displacement system. The drive of the gas displacement system, and thus the pumping rate, can take any deliberate time course in principle. As long as the negative pressure still does not reach the capillary negative pressure of the liquid in the sample pickup portion, the liquid cannot flow into the sample pickup portion. The second phase begins when liquid flows into the sample pickup portion. This moment is characterised through a crushed course of the pressure in the sample pickup portion against time. It is determined by comparing the gradient of the pressure-time curve at different time intervals. The volume that has flown in thereafter results from the following decrease of the negative pressure. In the case that the gas displacement system is operated further, the decrease of the negative pressure is related to the fictional increase of the negative pressure on account of the further operation of the gas displacement system without liquid flowing in. In the case that the gas displacement system is stopped, the decrease of the negative pressure is related to the negative pressure in the system at the moment of flowing in. The second phase ends at the moment in which the volume which is taken up corresponds to a predetermined value. As a consequence, the negative pressure applied by the gas displacement system is suddenly abated at the beginning of the third phase, as the case may be up to a keeping pressure which maintains the liquid in the sample pickup portion.

According to one form of realisation, the taken volume is determined according to $$\Delta v = p_E \cdot \text{apparatus parameter},$$

the apparatus parameter being apt to be determined by different methods:
i) according to the ideal gas law there is yielded at the moment of inflow:

$$\Delta v = -v_E \cdot \frac{\Delta p}{p_E + p_O} \text{ and therefrom:}$$

$$\text{apparatus parameter} = -\frac{v_E}{p_E + p_O}$$

ii) by knowing the drive speed or the volume displacement rate of the gas displacement system, respectively, before the moment of inflow $\Delta v^*$ und the pressure change rate $p_E$ before the moment of inflow the following is yielded:

$$\text{apparatus parameter} = \frac{\Delta v^*}{p_E}$$

wherein is valid either at continued monotonic operation of the drive $$\Delta p = p_E \Delta t + p_E - p \quad \text{(a)}$$

or when the drive is stopped $$\Delta p = p_E - p \quad \text{(b)}$$

with
$\Delta v$=taken volume
p=measured pressure
$v_E$=volume of gas displacement system and sample pickup portion at the moment of inflow
$p_E$=measured pressure at the moment of inflow
$p_E$=pressure change rate at the moment of inflow
$\Delta t$=time period after moment of inflow
$p_O$=absolute pressure.

The determination of the released liquid volume can be performed in different ways. In the case that the overall taken up volume is released in one single releasing step, the released liquid volume corresponds to the known taken liquid volumes. An additional detection of the released liquid volume at the time of release may be omitted. The determination of the flow parameters is performed via the taken volume, with the time duration after the moment of flowing in at the averaged negative pressure between the moment of flowing in and the end of taking up. Further, it is possible to determine the released liquid volume according to a method which has the aforementioned steps 1.2 to 1.6, an overpressure being applied to the sample pickup portion instead of the negative pressure in doing so. Preferably, the determination of the volume when releasing is performed according o a method which has the features 1.8 to 1.12 of claim 1. For this realisation of the method according to claim 2, the above explanations for the features 1.8 and 1.12 and for advantageous realisations of this method are valid.

Several realisations of the gas displacement system are incorporated into the methods according to the invention. In this it is dealt with a plunger which is movable in a cylinder, for dosing greater volumes in the milliliter and microliter range in particular. Further, pumping equipments are incorporated, which can be realised for dosing volumes in the milliliter to submicroliter range. Particularly incorporated are membrane displacement equipments, which have a membrane that limits the displacement volume and an actor assigned to it (a piezo bending converter, for instance).

The apparatus for dosing liquid volumes according to the invention comprises
12.1 a sample pickup portion with a pickup volume, the boundary of which is perforated with a liquid passage guiding to the outside and a gas passage,
12.2 a gas displacement system with a drive, which can be connected to the gas passage,
12.3 a sensor for measuring the negative pressure in the gas displacement system or in the sample pickup portion, and
12.4 an electric control unit, connected to the drive and the sensor, for actuating the drive such that a negative pressure is suddenly applied to the gas passage and is controlled to a constant working negative pressure, the taken volume is detected with the aid of the readjusted driving path, the determined taken volume is compared with a predetermined value of the volume that has to be taken, the drive is suddenly set out of operation when the taken volume has reached the predetermined value, one or several flow parameter(s) are determined from the values of the taken volume, the working negative pressure and the duration for picking up the volume, the drive is actuated for applying an overpressure to the sample pickup portion, the moment is determined at which a volume that has to be released must be released with the aid of the flow parameter(s) and the overpressure, and the drive is suddenly switched off when that moment is reached.

The apparatus for dosing liquid volumes according to the invention comprises
13.1 a sample pickup portion with a pickup volume, the boundary of which is perforated with a liquid passage guiding to the outside and a gas passage, 13.2 a gas displacement system with a drive, which can be connected to the gas passage, 13.3 a sensor for measuring the negative pressure, apt to be connected with the gas displacement system or the sample pickup portion, 13.4 an electric control unit, connected to the drive and the sensor, for switching on the drive such that a monotonically increasing negative pressure is applied to the gas passage, determining from the course of the negative pressure the moment of the inflow of liquid into the sample pickup portion, determining an apparatus parameter at the moment of the inflow of liquid, determining the taken liquid volume on account of the apparatus parameter either (a) at continued monotonic operation of the drive on account of the difference between the negative pressure that is calculated from the actual pumping rate and the time passed since the inflow of the liquid, and the actual negative pressure, or (b) when the drive is stopped at the moment of inflow of the liquid, on account of the difference between the negative pressure at the moment of inflow and the actually measured negative pressure, comparing the detected taken volume with a predetermined value and suddenly stopping the drive when the taken volume has reached the predetermined value.

BRIEF DESCRIPTION OF THE VIEWS OF THE DRAWINGS

The invention is hereinafter explained in more detail by means of the appended drawing of one example of its realisation. In the drawing shows.

DETAILED DESCRIPTION OF THE INVENTION

Figure 1:
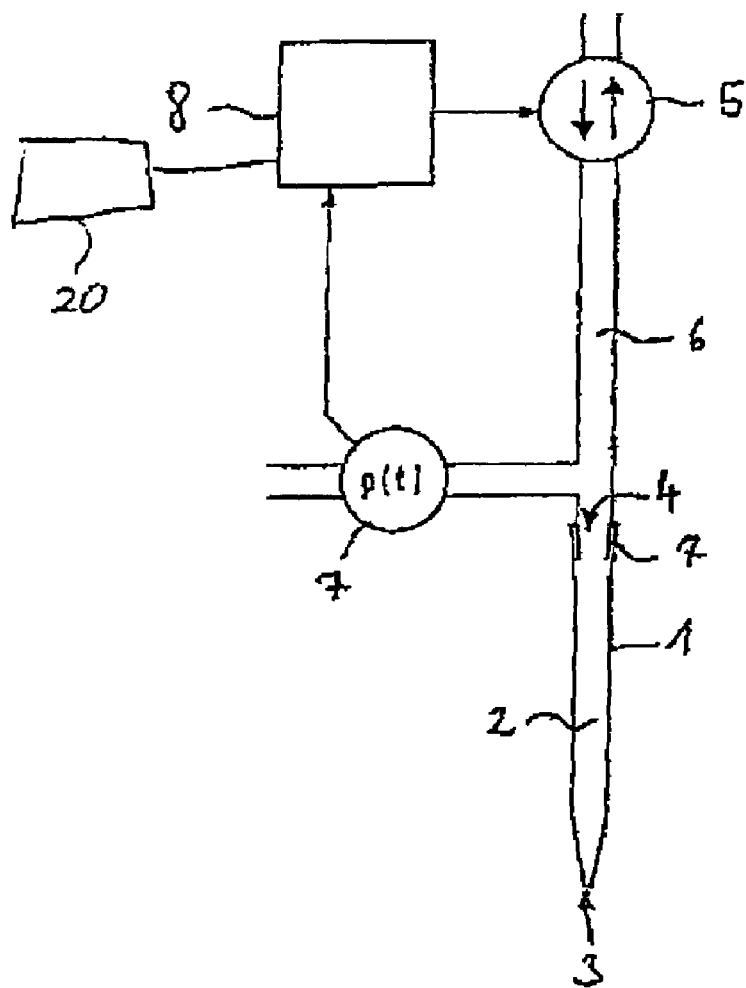
FIG. 1 an apparatus for dosing liquid volumes in a roughly schematic representation.

While this invention may be embodied in many different forms, there are described in detail herein a specific preferred embodiment of the invention. This description is an exemplification of the principles of the invention and is not intended to limit the invention to the particular embodiment illustrated According to FIG. 1, the apparatus for dosing has a sample pickup portion 1, which is realised as a pipette point. The tube-like sample pickup portion 1 has a pickup volume 2 in the inside, a liquid passage 3 connecting the pickup volume with the surroundings on a bottom conical end and a gas passage that leads from the pickup volume 2 to the exterior, on a slightly conical extended upper end.

Further, there is a gas displacement system with a bidirectional pump 5, which is connected with a neck 7 for putting up the conical extended end of the sample pickup portion 1 via a connection channel 6.

The pumping equipment 5 is for instance a (micro-) membrane pump, a plunger stroke equipment or a membrane arrangement with a piezo actor, e.g.

A pressure sensor 7 is attached to the connection channel 6.

Furthermore, an electric control unit 8 is connected, which is itself electrically connected to the pumping equipment 5 and the pressure sensor 7.

In a first mode of operation, the pump 5 is suddenly or with the maximum negative pumping rate, respectively, put into operation by the electric control unit 8 after dipping the liquid passage 3 into a liquid, in order to hit a certain working negative pressure in the connection channel 6 and the working volume 2 as fast as possible. The volume of liquid which flows in through the liquid passage 3 in doing so can be neglected.

Further, the control unit 8 controls the pumping device 5 such that the negative pressure which is measured by the pressure sensor 7 corresponds to the predetermined negative working pressure as accurately as possible. The volume of liquid flowing through the liquid passage 3 in this phase is proportional to the driving path of the drive of the pumping device 5. When piezo actors are used, for instance, the driving path is proportional to the control voltage Δu that is applied by the control unit 8.

With the aid of this control voltage Δu, the electric control unit 8 determines the respective taken volume and compares it with a predetermined value of the volume that has to be taken up. At sufficient correspondence, the control unit 8 suddenly stops the pumping device, for instance by keeping the voltage on the piezo actor unchanged. At stopped pumping device 5, no further liquid flows in through the liquid passage 3. The volume of liquid which still flows in at the phase of stopping the pumping device 5 can be neglected.

Further, when taking up the liquid, the control unit 8 determines, on account of the liquid that is taken up Δv and the duration for taking up the liquid Δt, a flow parameter S for the corresponding negative working pressure p. This is defined as follows:

$S = \Delta v / \Delta t$ at the pressure $p$

For the release, the sample pickup portion 1 with the liquid passage 3 is directed towards a release location (in a laboratory vessel or in an accommodation of a microtiter plate, e.g.). The control unit 8 controls the pumping device 5 such that an overpressure is generated in the connection channel 6 and in the pickup volume 2, which pushes out the liquid that was taken up through the liquid passage channel 3. Preferably, the release of the liquid takes place in a free stream, the overpressure being selected correspondingly high.

When releasing, the control unit 8 determines the moment Δt, at which the volume Δv that has to be released is released, on account of the flow parameter S and the predetermined or measured overpressure p. At constant overpressure, the moment Δt can be easily determined with the aid of the above definitions. When the pressure changes in the course of the release, the volumes which were released at measured pressure conditions in time intervals are integrated. The moment when the volume that is to be released is released is reached when the integrated volume corresponds to the volume that is to be released.

When the moment is reached, the control unit 8 suddenly stops the pumping device 5. The liquid volume which will then still flow out is negligible. The early stopping of the pumping device 5 by the control unit 8 is incorporated in order to compensate the flowing out of liquid in the phase of stopping down the pumping device 5.

According to another mode of operation, the control unit 8 puts the pumping device 5 into operation after dipping in the liquid passage 3, so that a negative pressure is generated in the pickup volume 2, which increases monotonically. The phase of the monotonic increase of the negative pressure in the pickup portion 2 is shown between points 1 and 2 in FIG. 2. In this phase, liquid still does not penetrate into the liquid passage 3 on account of wetting and capillary forces.

Figure 2:
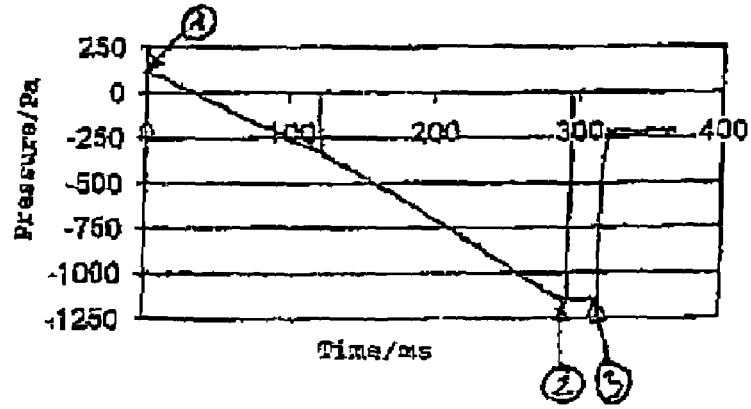
FIG. 2 a pressure curve in a pressure-time diagram when liquid is picked up.

The invasion of liquid is characterised by a crushing of the pressure curve, as is shown in the region of the pressure curve between the points 2 and 3 of FIG. 2. The control unit 8 determines the moment of the inflow of the liquid 2 by repeated comparison of the gradient of the pressure curve in consecutive curve portions.

After the moment of flowing in, the pumping device 5 can be operated further by the control unit 8 with the same pumping rate as before. When the pumping device 5 is operated by the control unit 8 with constant pumping rate $\dot{p}_E$ after the moment of the inflow, a pressure difference $\Delta p$ between the extrapolated pressure curve and the measured pressure p results at each moment between the points 2 and 3.

When the pumping device 5 is switched off by the control unit 8 at the moment of inflow 2, a pressure difference $\Delta p$ between the pressure $p_E$ measured at the moment of inflow and the pressure p measured later can be determined for each following moment.

With the aid of the pressure difference $\Delta p$, the gas volume in the connection channel 6 and in the pickup volume 2 and the measured pressure $p_E$ at the moment of inflow, the taken volume $\Delta V$ of the liquid can be calculated by the control unit in the following manner.

$$\Delta v = \Delta p \cdot \text{apparatus parameter}$$

The release of liquid takes place with the aid of the flow parameter S, as has been explained for the first described mode of operation.

Reference numeral 20 in FIG 1. is an acoustic speech output device, which is electrically connected to the electric control unit. The acoustic speech output device emits messages which fit to different working procedures. The acoustic speech output device is realized by piezo actors or membrane actors.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Method for dosing liquid volumes, wherein a sample pickup portion with a pickup volume, the boundary of which is perforated with a liquid passage guiding to the outside and a gas passage, is dipped into a liquid with the liquid passage, a negative pressure is suddenly applied to the gas passage, which is generated by a gas displacement system, a drive of the gas displacement system is readjusted such that a constant negative working pressure exists in the sample pickup portion, the taken sample volume is detected with the aid of the readjusted drive, the detected taken volume is compared with a predetermined value of the volume that is to be taken, when the predetermined value is reached by the taken volume, the negative pressure applied on the sample pickup portion is suddenly abated, the sample pickup portion with the liquid passage is pulled out of the liquid, the sample pickup portion with the liquid passage is directed towards a releasing location, one or more flow parameters is/are determined from the values of the taken volume, the negative working pressure and the time period required to take up the volume, an overpressure is applied to the gas passage of the sample pickup portion, the moment at which a volume that is to be released is released is determined with the aid of the flow parameter(s) and the overpressure, and when the moment is reached, the overpressure applied to the sample pickup portion is suddenly abated.

2. Method according to claim 1, wherein the moment when the volume is released is determined by means of the flow parameter(s), a constant overpressure and the volume that has to be released.

3. Method according to claim 1, wherein the volume released is determined by means of the flow parameter(s), the respective present overpressure and the respective action duration of the overpressure, and the moment at which the volume is to be released is reached when the determined volume corresponds to the released one.

4. Method according to claim 1, wherein in the determination of the moment at which the volume is released, the dependence of the outflow characteristic of the sample pickup portion is taken into account according to a reference-pressure-volume curve.

5. Method according to claim 1, in which the negative pressure when picking up and/or the overpressure when releasing liquid is/are selected such that when picking up and/or releasing into/from the sample pickup portion, interfacial and/or frictional effects are overcome.

6. Method according to claim 1, in which the overpressure when releasing is selected such that the liquid is released in a free stream from the sample pickup portion.

7. Method according to claim 1, in which the taken liquid is released in several part steps from the sample pickup portion.

8. Apparatus for dosing liquid volumes, comprising a sample pickup portion with a pickup volume, the boundary of which is perforated with a liquid passage guiding to the outside and a gas passage, a gas displacement system with a drive, which can be connected to the gas passage, a sensor for measuring the negative pressure in the gas displacement system or in the sample pickup portion, and an electric control unit, connected to the drive and the sensor, for actuating the drive such that a negative pressure is suddenly applied to the gas passage and is controlled to a constant working negative pressure, the taken volume is detected with the aid of a readjusted driving path, the determined taken volume is compared with a predetermined value of the volume that has to be taken, the drive is suddenly set out of operation when the taken volume has reached the predetermined value, one or several flow parameter(s) are determined from the values of the taken volume, the working negative pressure and the duration for picking up the volume, the drive is actuated for applying an overpressure to the sample pickup portion, the moment is determined at which a volume that has to be released must be released with the aid of the flow parameter(s) and the overpressure, and the drive is suddenly switched off when that moment is reached.

9. Apparatus according to claim 8, wherein the electric control unit determines the moment at which the volume is released by means of the flow parameter(s), a constant overpressure and the volume that has to be released.

10. Apparatus according to claim 8, wherein the electric control unit determines the volume released by means of the flow parameter(s), the overpressure detected by the pressure sensor and the respective action duration of the overpressure, and puts the drive out of operation when the determined volume corresponds to the volume that is to be released.

11. Apparatus according to claim 8, wherein the electric control unit in the determination of the moment at which the volume is released, takes into account the dependence of the outflow characteristic of the sample pickup portion according to a reference-pressure-volume curve.

12. Apparatus according to claim 8, wherein the electric control unit controls the drive such that the negative pressure when picking up and/or the overpressure when releasing overcomes interfacial and/or frictional effects when picking up and/or releasing liquids.

13. Apparatus according to claim 8, wherein the electric control unit controls the drive such that the overpressure when releasing drives out the liquid in a free stream from the sample pickup portion.

14. Apparatus according to claim 8, wherein the electric control unit controls the drive such that taken liquid is released in part steps from the sample pickup portion.

15. Apparatus according to claim 8, wherein the electric control unit is provided with an acoustic speech output.

16. Apparatus according to claim 15, wherein the acoustic speech output emits messages which fit to different working procedures.

17. Apparatus according to claim 15, wherein the acoustic speech output is realised by piezo actors or membrane actors.

* * * * *